(12) United States Patent
Taylor et al.

(10) Patent No.: US 8,067,658 B2
(45) Date of Patent: Nov. 29, 2011

(54) ISOMERIZATION PROCESS

(75) Inventors: Bradley M. Taylor, Tulsa, OK (US); David E. Simon, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 317 days.

(21) Appl. No.: 12/358,632

(22) Filed: Jan. 23, 2009

(65) Prior Publication Data

US 2010/0191032 A1  Jul. 29, 2010

(51) Int. Cl.
C07C 5/22  (2006.01)

(52) U.S. Cl. ........................................ 585/750; 585/751

(58) Field of Classification Search .................. 585/750, 585/751

See application file for complete search history.

(56) References Cited

U.S. PATENT DOCUMENTS

| | | |
|---|---|---|
| 3,067,127 A | 12/1962 | Plank et al. |
| 3,558,471 A | 1/1971 | Kittrell |
| 4,912,077 A | 3/1990 | Lachman et al. |
| 5,510,309 A | 4/1996 | Chang et al. |
| 5,552,128 A | 9/1996 | Chang et al. |
| 5,854,170 A | 12/1998 | Chang et al. |
| 6,080,904 A | 6/2000 | Chang et al. |
| 6,124,232 A | 9/2000 | Chang et al. |
| 6,184,430 B1 | 2/2001 | Venkatesh et al. |
| 6,977,322 B2 | 12/2005 | Gillespie |
| 7,304,199 B2 | 12/2007 | Xu et al. |
| 7,399,896 B2 | 7/2008 | Gillespie et al. |
| 2003/0181774 A1 | 9/2003 | Kong et al. |

*Primary Examiner* — Thuan Dinh Dang

(57) ABSTRACT

An isomerization process is disclosed including contacting a n-hexane hydrocarbon feed containing less than about 10 volume % naphthenic hydrocarbons with a catalyst to produce an iso-hexane containing product; wherein the catalyst is prepared by: a) incorporating tungsten on a zirconium hydroxide solid; b) drying and calcining the tungsten impregnated zirconium hydroxide; c) sizing the dried and calcined material to particle sizes between about 150 and about 600 microns; d) incorporating a Group VIII metal selected from the group consisting of nickel, platinum and palladium, and combinations thereof, on the sized material; e) drying and calcining the Group VIII metal impregnated tungsten/zirconia material; and f) contacting the second dried and calcined material with hydrogen in a reducing environment to form the catalyst which contains tungsten, zirconia and a Group VIII metal selected from the group consisting of nickel, platinum and palladium, and combinations thereof.

20 Claims, 16 Drawing Sheets

US 8,067,658 B2

ISOMERIZATION PROCESS

The present invention relates to a process for the isomerization of n-hexane. In another aspect, this invention relates to a process for the isomerization of n-hexane with a catalyst containing tungsten, zirconium and a Group VIII metal.

One way to comply with the regulations limiting benzene concentration in gasoline is to hydrogenate benzene forming cyclohexane, which has a much lower octane number than benzene, and results in an octane penalty for the resulting product as compared to the benzene feed. To compensate for this loss of octane, n-hexane, present in many refinery streams including the benzene hydrogenation product, can be isomerized to higher octane iso-hexanes.

Therefore, development of an improved process for effectively isomerizing n-hexane to higher octane iso-hexanes would be a significant contribution to the art, greatly increasing the value of the n-hexane hydrocarbons and countering the octane loss from hydrogenating benzene.

BRIEF SUMMARY OF THE INVENTION

In accordance with the present invention, an isomerization process is provided including the following:

contacting a hydrocarbon feed comprising n-hexane and less than about 10 volume % naphthenic hydrocarbons with a catalyst at isomerization conditions for isomerization of at least a portion of the n-hexane to a product comprising iso-hexane; wherein the catalyst is prepared by the following method:

(a) incorporating tungsten on a zirconium hydroxide solid by incipient wetness impregnation using an aqueous solution of a tungsten compound to form tungsten impregnated zirconium hydroxide;

(b) drying and calcining the tungsten impregnated zirconium hydroxide to form a first dried and calcined material;

(c) sizing the dried and calcined material to particle sizes between about 150 and about 600 microns to form a sized material;

(d) incorporating a Group VIII metal selected from the group consisting of nickel, platinum and palladium, and combinations thereof, on the sized material by incipient wetness impregnation using an aqueous solution of a Group VIII metal compound comprising said Group VIII metal to form a Group VIII metal impregnated tungsten/zirconia material;

(e) drying and calcining the Group VIII metal impregnated tungsten/zirconia material to form a second dried and calcined material; and (f) contacting the second dried and calcined material with hydrogen in a reducing environment to form the catalyst which comprises tungsten, zirconia and a Group VIII metal selected from the group consisting of nickel, platinum and palladium, and combinations thereof.

DETAILED DESCRIPTION OF THE INVENTION

Figure 1:
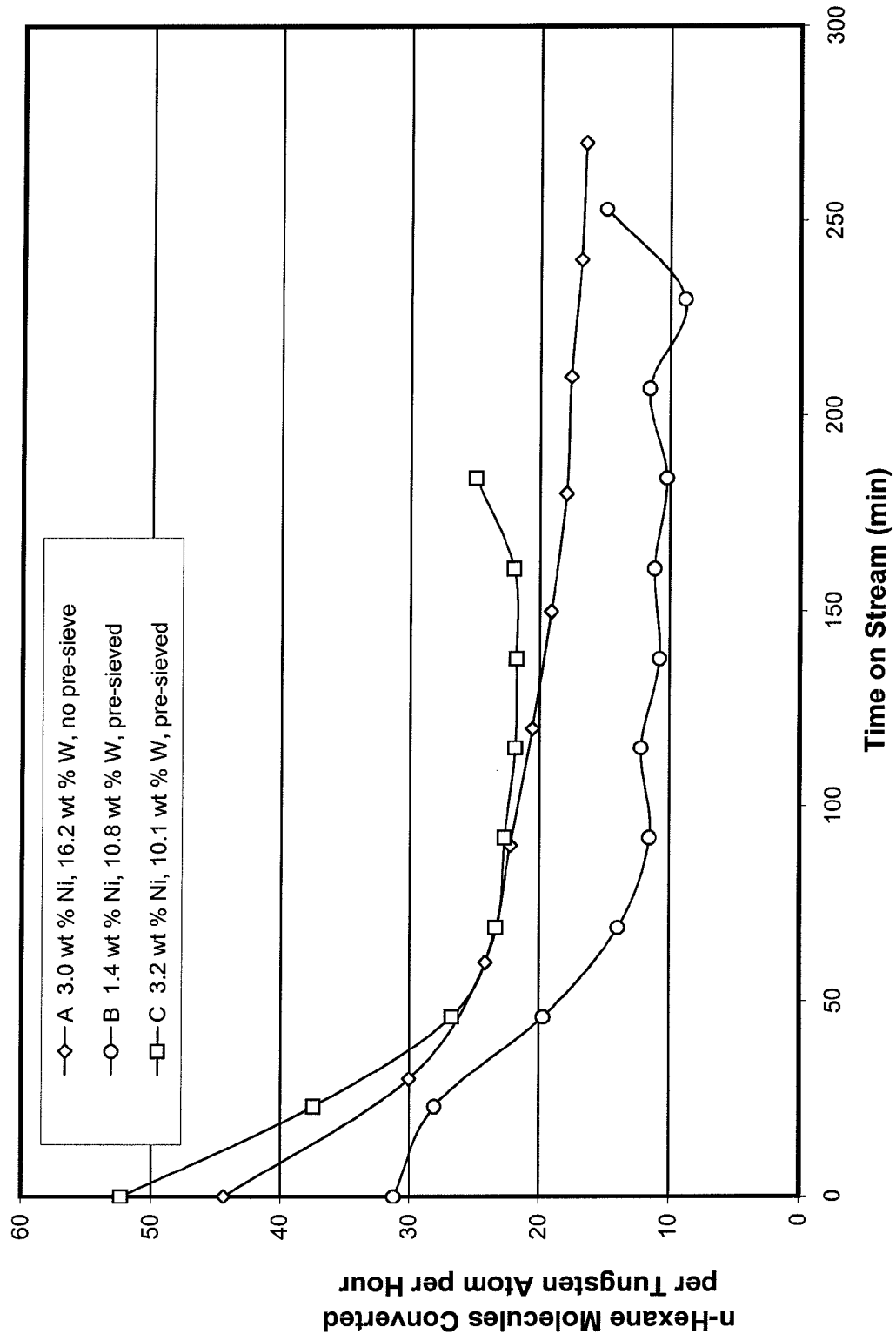
FIG. 1 is a graphic illustration of n-Hexane Molecules Converted per Tungsten Atom per Hour vs. Time on Stream data for three runs wherein nickel containing catalysts were separately used to convert n-hexane.

The hydrocarbon feed stream of this invention can be any hydrocarbon feed comprising, consisting of, or consisting essentially of n-hexane and less than about 10 volume % naphthenic hydrocarbons, and more preferably less than about 5 volume % naphthenic hydrocarbons. Preferably, the hydrocarbon feed comprises at least about 80 weight % n-hexane, and more preferably at least about 90 weight % n-hexane. Naphthenic hydrocarbons can include any mono or poly cyclic hydrocarbon. Most typically, the naphthenic hydrocarbon in a n-hexane stream is cyclohexane.

The hydrocarbon feed stream is contacted with a material comprising, consisting of, or consisting essentially of a catalyst, at isomerization conditions, for isomerization of at least a portion of the n-hexane to a product comprising, consisting of, or consisting essentially of iso-hexanes. The product preferably comprises, consists of, or consists essentially of an iso-hexane selected from the group consisting of 2,2-dimethylbutane, 2,3-dimethylbutane, 2-methylpentane, 3-methylpentane, and combinations thereof. The product more preferably comprises, consists of, or consists essentially of 2,3-dimethylbutane.

The isomerization conditions include a temperature in the range of from about 160° C. to about 300° C., a pressure in the range of from about 150 to about 250 psig, a liquid hourly space velocity of about 0.5 to about 20 $hr^{-1}$, and a hydrogen to hydrocarbon molar ratio of at least about 0.1; preferably a temperature in the range of from about 177° C. to about 288° C., a pressure in the range of from about 190 to about 210 psig, a liquid hourly space velocity of about 0.5 to about 10 $hr^{-1}$, and a hydrogen to hydrocarbon molar ratio of at least about 0.5; and more preferably a temperature in the range of from about 177° C. to about 230° C., a pressure in the range of from about 190 to about 210 psig, a liquid hourly space velocity of about 0.5 to about 4 $hr^{-1}$, and a hydrogen to hydrocarbon molar ratio of at least about 0.5.

The catalyst is preferably prepared by the following method:
  (a) incorporating tungsten on a zirconium hydroxide solid by incipient wetness impregnation using an aqueous solution of a tungsten compound to form tungsten impregnated zirconium hydroxide;
  (b) drying and calcining the tungsten impregnated zirconium hydroxide to form a first dried and calcined material;
  (c) sizing the dried and calcined material to particle sizes between about 150 and about 600 microns to form a sized material;
  (d) incorporating a Group VIII metal selected from the group consisting of nickel, platinum and palladium, and combinations thereof, on the sized material by incipient wetness impregnation using an aqueous solution of a Group VIII metal compound comprising the Group VIII metal to form a Group VIII metal impregnated tungsten/zirconia material;
  (e) drying and calcining the Group VIII metal impregnated tungsten/zirconia material to form a second dried and calcined material; and
  (f) contacting the second dried and calcined material with hydrogen in a reducing environment to form the catalyst which comprises, consists of, or consists essentially of tungsten, zirconia and a Group VIII metal selected from the group consisting of nickel, platinum and palladium, and combinations thereof.

The tungsten compound can be any tungsten compound capable of becoming a part of an aqueous solution, and is preferably ammonium metatungstate.

The calcining of step b) is in the presence of oxygen and at a temperature in the range of from about 600° C. to about 900° C., preferably from about 700° C. to about 815° C. The calcining of step e) is in the presence of oxygen and at a temperature in the range of from about 300° C. to less than or equal to about the calcining temperature in step b). The reducing environment of step (f) preferably comprises a temperature in the range of from about 350 to about 400° C., and a pressure in the range of from about 150 psig to about 250 psig.

The Group VIII metal compound can be any compound capable of becoming a part of an aqueous solution, and is preferably selected from the group consisting of nickel(II) nitrate, chloroplatinic acid, tetraamine palladium(II)nitrate, diammineplatinum(II)nitrate, palladium(II)nitrate, and combinations thereof.

For catalysts wherein the Group VIII metal compound comprises nickel; the molar ratio of nickel to tungsten in the second dried and calcined material in step (e) is at most about 0.65; and at least about 70% of the nickel of the second dried and calcined material is in the form of nickel tungstate.

Preferably, the catalyst comprises between about 60 and about 95 weight % zirconia, more preferably between about 70 and about 90 weight % zirconia, and most preferably between about 75 and about 90 weight % zirconia; and between about 5 and about 40 weight % tungsten, more preferably between about 5 and about 35 weight % tungsten, and most preferably between about 10 and about 20 weight % tungsten; and between about 0.01 and about 5 weight % of the Group VIII metal, more preferably between about 0.1 and about 5 weight % of the Group VIII metal.

For catalysts wherein the Group VIII metal compound comprises nickel, the catalyst preferably comprises between about 1.5 and about 5 weight % nickel. For catalysts wherein the Group VIII metal, of the Group VIII metal compound, is selected from the group consisting of platinum, palladium, or combinations thereof, the catalyst preferably comprises between about 0.1 and about 0.5 weight % of the Group VIII metal.

The zirconium hydroxide solid of step (a) can contain sufficient aluminum to result in the catalyst containing between about 0.1 and about 3 weight % aluminum.

The zirconium hydroxide solid of step (a) can also contain sufficient hafnium to result in the catalyst containing between about 0.1 and about 2 weight % hafnium.

The catalyst can contain neither, either or both of such aluminum and hafnium components.

EXAMPLES

The following examples are presented to further illustrate the present invention and are not to be construed as unduly limiting the scope of the present invention.

Example I $WO_3/ZrO_2$ Preparation

The preparation began with the precipitation of amorphous $Zr(OH)_4$. Sufficient concentrated aqueous ammonium hydroxide was added drop-wise to a 0.25 molar aqueous solution of zirconyl chloride under vigorous stirring to obtain a final pH of 10.5-11. The resulting slurry was allowed to age for 1 hour under vigorous stirring before being filtered and washed with approximately 3 times its volume in distilled water. The filter cake was dried in a vacuum oven for 2 days at 121.1° C. and approximately −15 in. Hg. Once dry, the $Zr(OH)_4$ was washed a second time in approximately 3 times its volume of distilled water to ensure all of the residual chloride ions were rinsed from the solid. The $Zr(OH)_4$ was dried overnight in a vacuum oven at 121.11° C. and approximately −15 in. Hg. Tungsten was deposited on the zirconium hydroxide via incipient wetness impregnation using an aqueous solution of ammonium metatungstate (($NH_4)_6$ $H_2W_{12}O_{40}\cdot xH_2O$) added drop-wise to $Zr(OH)_4$ taken directly from the vacuum oven. The ammonium metatungstate solution concentration was adjusted depending on the desired wt. % W in the final material. The wetted support was dried overnight in a vacuum oven at 121.1° C. and approximately −15 in. Hg. The dried material was calcined in air for three hours at 748.9° C.

Control Ni/WO₃/ZrO₂ Catalyst "A"
---
(3.0 wt. % Ni; 16.2 wt. % W)

Nickel was added by incipient wetness impregnation to a portion of the WO₃/ZrO₂ that had been dried overnight in a vacuum oven (121.1° C., ~−15 in. Hg) using an aqueous solution of nickel (II) nitrate. The nickel (II) nitrate solution concentration was adjusted depending on the desired wt. % Ni in the final material. The catalyst was again dried overnight in a vacuum oven (121.1° C., ~−15 in. Hg) before being calcined at 498.9° C. for 3 hours in air. Prior to evaluation for hexane conversion, the catalyst was exposed to 120 standard cubic centimeters per minute (sccm) hydrogen at 371.1° C. and 200 psig for one hour.

Inventive Ni/WO₃/ZrO₂ Catalyst "B"
---
(1.4 wt. % Ni; 10.8 wt. % W)

and

Inventive Ni/WO₃/ZrO₂ Catalyst "C"
---
(3.2 wt. % Ni; 10.1 wt. % W)

Catalysts B and C were prepared in the same manner as that described for the preparation of Catalyst A except that for inventive Catalysts B and C the calcined support materials were sized to 35-100 mesh (resulting in particle sizes ranging between about 150 and about 600 microns) prior to the addition of Nickel.

Catalysts A, B and C were evaluated for the isomerization of n-hexane by the following procedure:

A stream of hydrocarbons containing about 5 wt % cyclohexane in n-hexane was separately passed over about two grams of each of Catalysts A, B and C in a reactor at a rate of about 25 mL/hr (a LHSV of about 17 hr⁻¹). Along with the hydrocarbon feed, about 60 sccm of H₂ was also charged to the reactor during each run, resulting in a H₂/HC molar ratio of about 0.7. The reactor temperature was about 287.8° C. and the pressure was about 200 psig.

The results, expressed as n-hexane molecules converted per tungsten atom per hour versus time on stream, are presented in FIG. 1. The results demonstrate that the activities of pre-sieved Inventive Catalysts B and C stabilized, while the activity of non pre-sieved Control Catalyst A continually decreased with time on stream.

Example II

Inventive Pt/WO₃/ZrO₂ Catalyst "D"
---
(0.5 wt. % Pt; 12.0 wt. % W)

Catalyst D was prepared using the same procedure as that for Catalyst B, but, in place of the aqueous solution of nickel (II) nitrate, using an aqueous solution of chloroplatinic acid.

Control Pt/Mordenite Catalyst "E"
---
(0.5 wt. % Pt)

A quantity of mordenite was contacted with an aqueous solution of chloroplatinic acid. The catalyst was dried overnight in a vacuum oven (121.1° C., ~−15 in. Hg) before being calcined at 498.9° C. for 3 hours in air. Prior to evaluation for hexane conversion, the catalyst was exposed to 120 sccm hydrogen at 371.1° C. and 200 psig for one hour.

Control Pt/ZSM-5 Catalyst "F"
---
(0.5 wt. % Pt)

Catalyst F was prepared using the same procedure as that for Catalyst E, but, in place of the Mordenite, using a ZSM-5 material.

A stream of hydrocarbons containing about 5 wt % cyclohexane in n-hexane was separately passed over about eight grams of each of Catalysts D, E and F in a reactor at a rate of about 25 mL/hr (a LHSV of about 2 hr⁻¹). Along with the hydrocarbon feed, about 60 sccm of H₂ was also charged to the reactor during each run, resulting in a H₂/HC molar ratio of about 0.7. The reactor temperature varied from about 204.4° C. at the beginning of each run down to about 176.7° C. after 160 minutes on stream and the pressure was about 200 psig.

Figure 2:
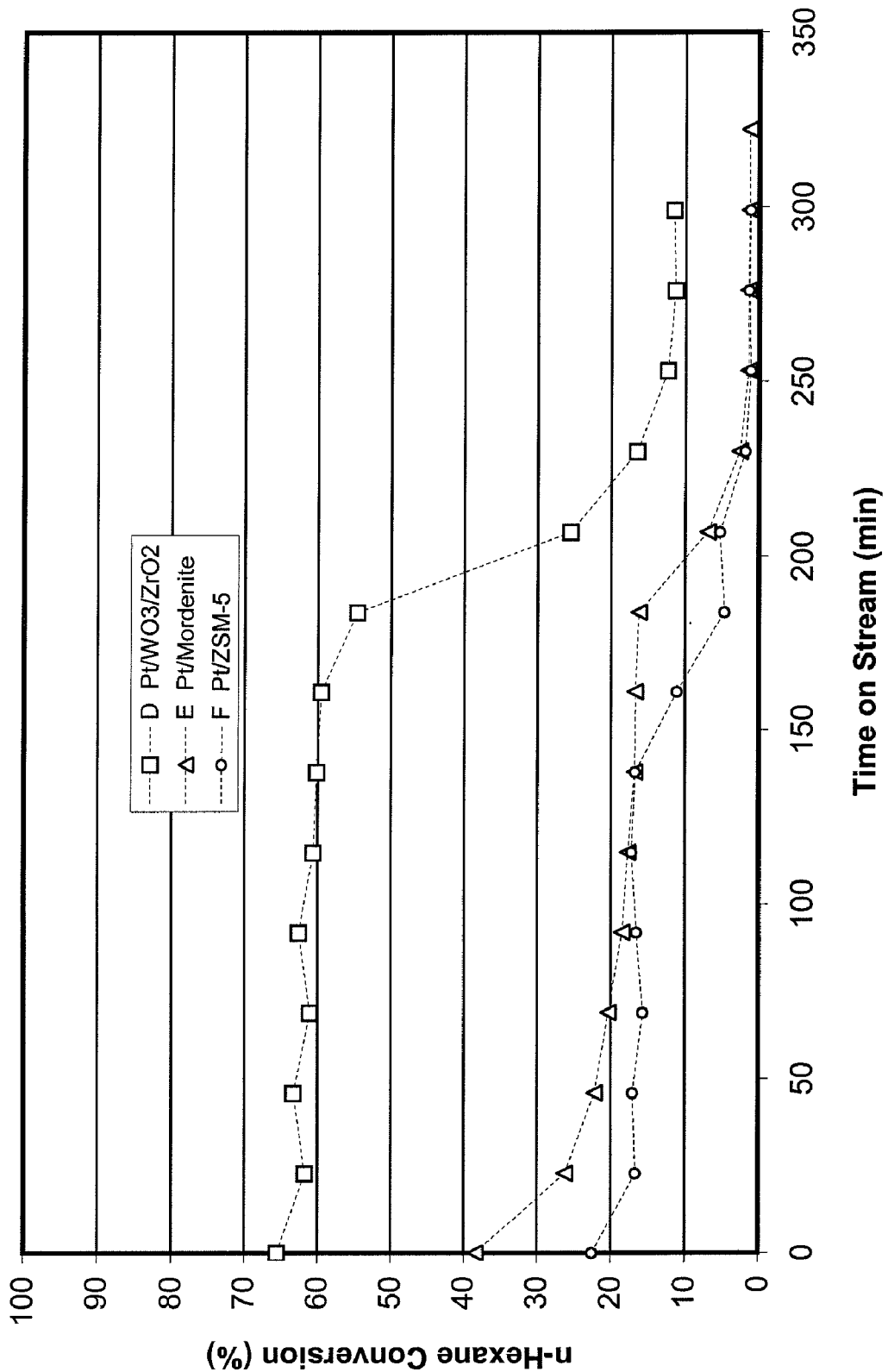
FIG. 2 is a graphic illustration of n-Hexane Conversion vs. Time on Stream data for three runs wherein platinum containing catalysts were separately used to convert n-hexane.
Figure 3:
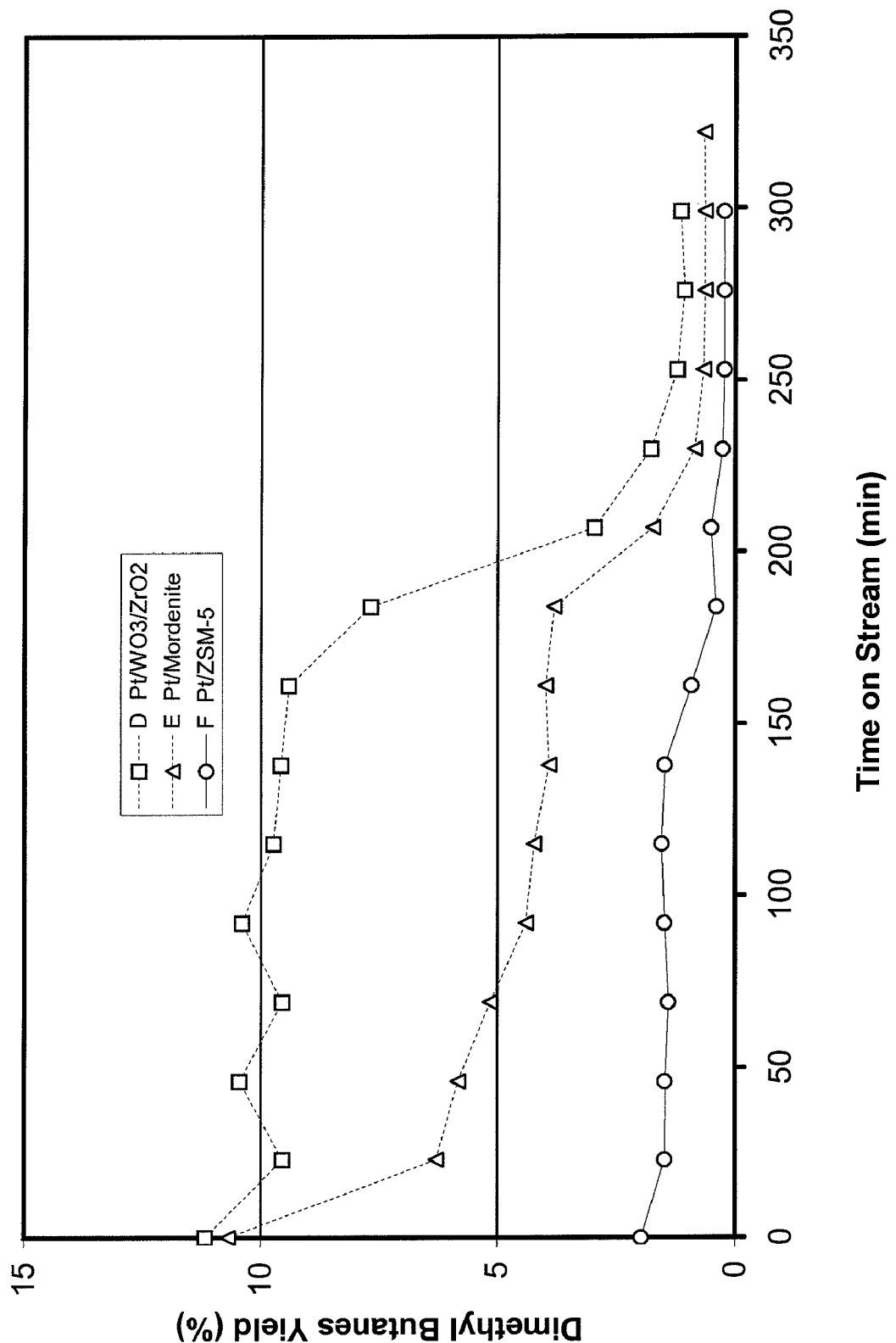
FIG. 3 is a graphic illustration of Dimethyl Butanes Yield vs. Time on Stream data for three runs wherein platinum containing catalysts were separately used to convert n-hexane.
Figure 4:
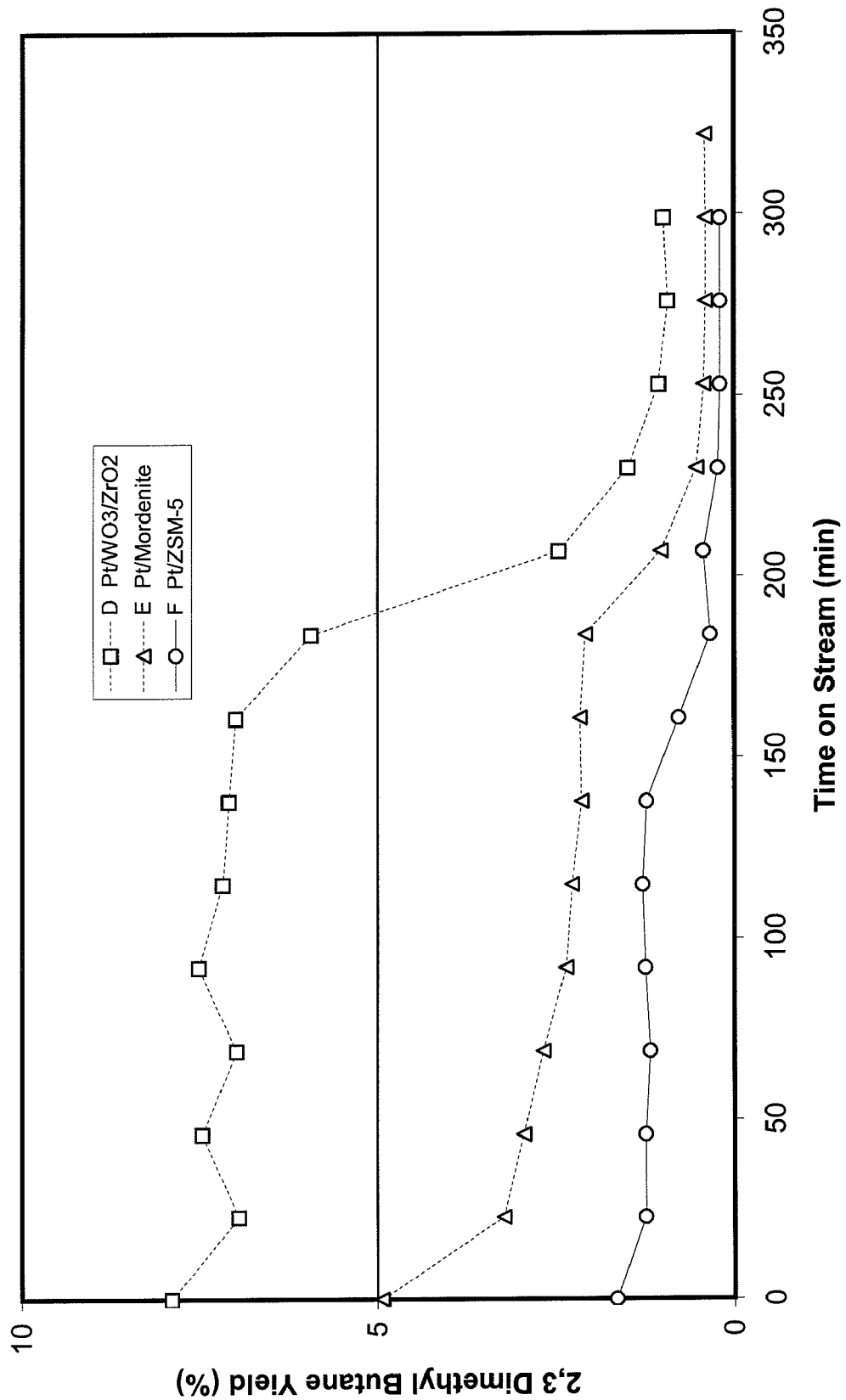
FIG. 4 is a graphic illustration of 2,3 Dimethyl Butane Yield vs. Time on Stream data for three runs wherein platinum containing catalysts were separately used to convert n-hexane.

Conversion results, expressed as n-hexane conversion versus time on stream, are presented in FIG. 2, results of dimethylbutanes (DMB) yield versus time on stream are presented in FIG. 3, and results of 2,3 DMB yield versus time on stream are presented in FIG. 4. The results in FIGS. 2-4 demonstrate that the inventive Pt/WO₃/ZrO₂ Catalyst D is much more effective at converting n-hexane, with much higher DMB and 2,3 DMB yields, than the Pt/Mordenite Control Catalyst E or the Pt/ZSM-5 Control Catalyst F.

Example III

Inventive Pt/WO₃/ZrO₂ Catalyst "G"
---
(0.3 wt. % Pd; 13.0 wt. % W)

Catalyst G was prepared using the same procedure as that for Catalyst B, but, in place of the aqueous solution of nickel (II) nitrate, using an aqueous solution of tetraamine palladium (II) nitrate.

Control Pd/Mordenite Catalyst "H"
---
(0.3 wt. % Pd)

Catalyst H was prepared using the same procedure as that for Catalyst E, but, in place of the aqueous solution of chloroplatinic acid, using an aqueous solution of tetraamine palladium (II) nitrate.

Control Pd/ZSM-5 Catalyst "I"
---
(0.3 wt. % Pd)

Catalyst I was prepared using the same procedure as that for Catalyst F, but, in place of the aqueous solution of chloroplatinic acid, using an aqueous solution of tetraamine palladium (II) nitrate.

A stream of hydrocarbons containing about 5 wt % cyclohexane in n-hexane was separately passed over about eight grams of each of Catalysts G, H and I in a reactor at a rate of about 25 mL/hr (a LHSV of about 2 hr$^{-1}$). Along with the hydrocarbon feed, about 60 sccm of $H_2$ was also charged to the reactor during each run, resulting in a $H_2$/HC molar ratio of about 0.7. The reactor temperature varied from about 204.4° C. at the beginning of each run down to about 176.7° C. after 160 minutes on stream and the pressure was about 200 psig.

Figure 5:
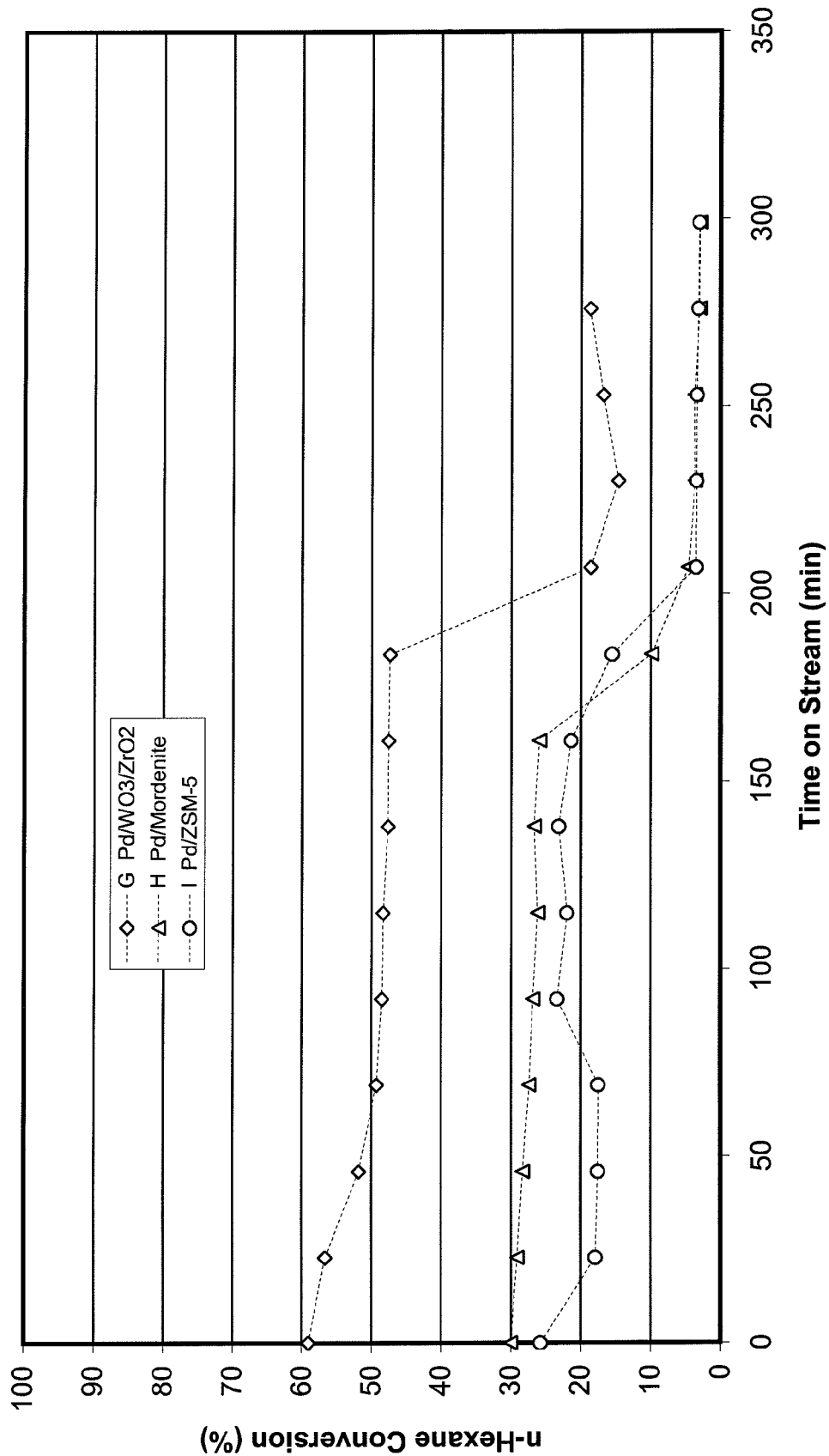
FIG. 5 is a graphic illustration of n-Hexane Conversion vs. Time on Stream data for three runs wherein palladium containing catalysts were separately used to convert n-hexane.
Figure 6:
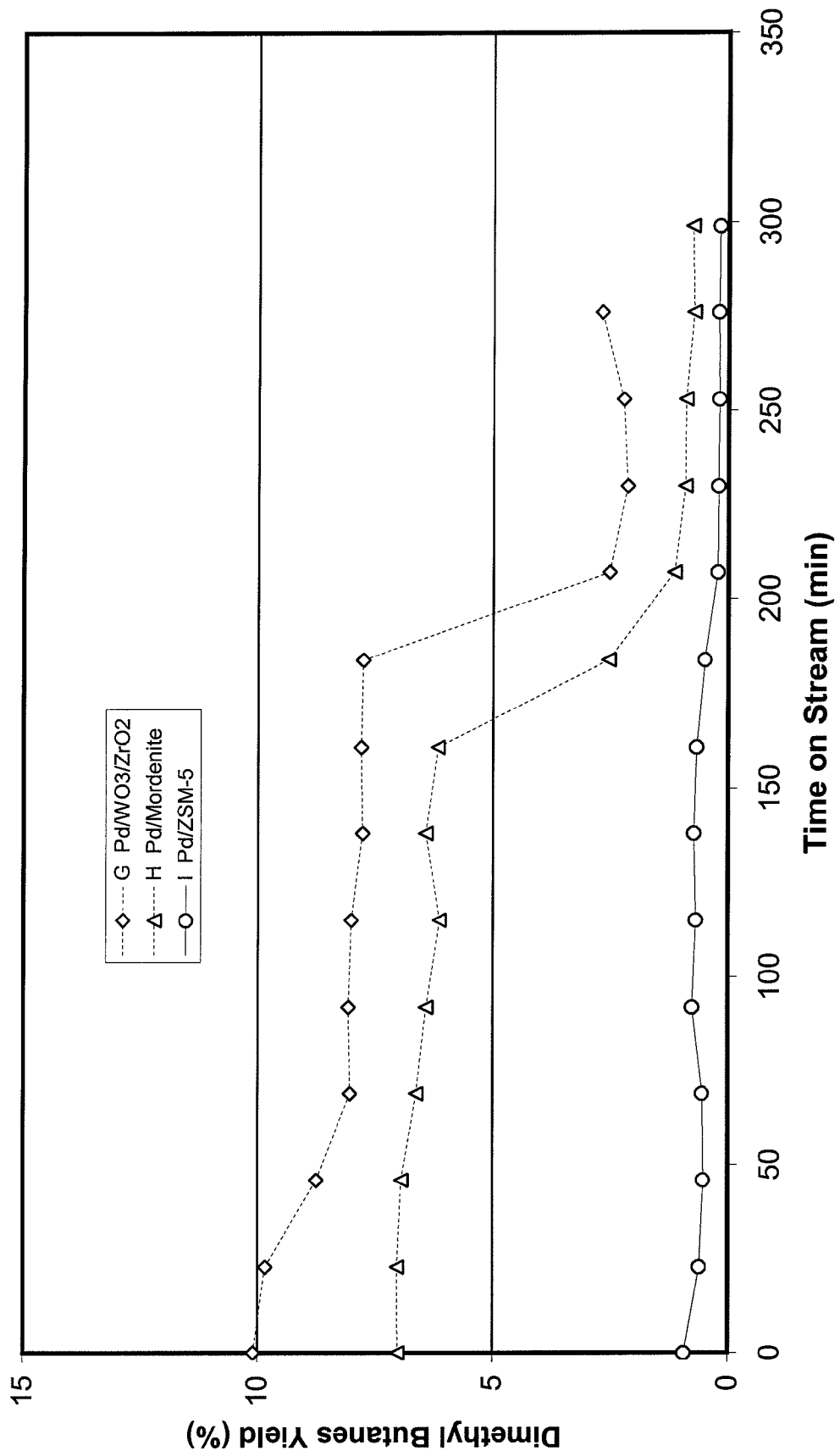
FIG. 6 is a graphic illustration of Dimethyl Butanes Yield vs. Time on Stream data for three runs wherein palladium containing catalysts were separately used to convert n-hexane.
Figure 7:
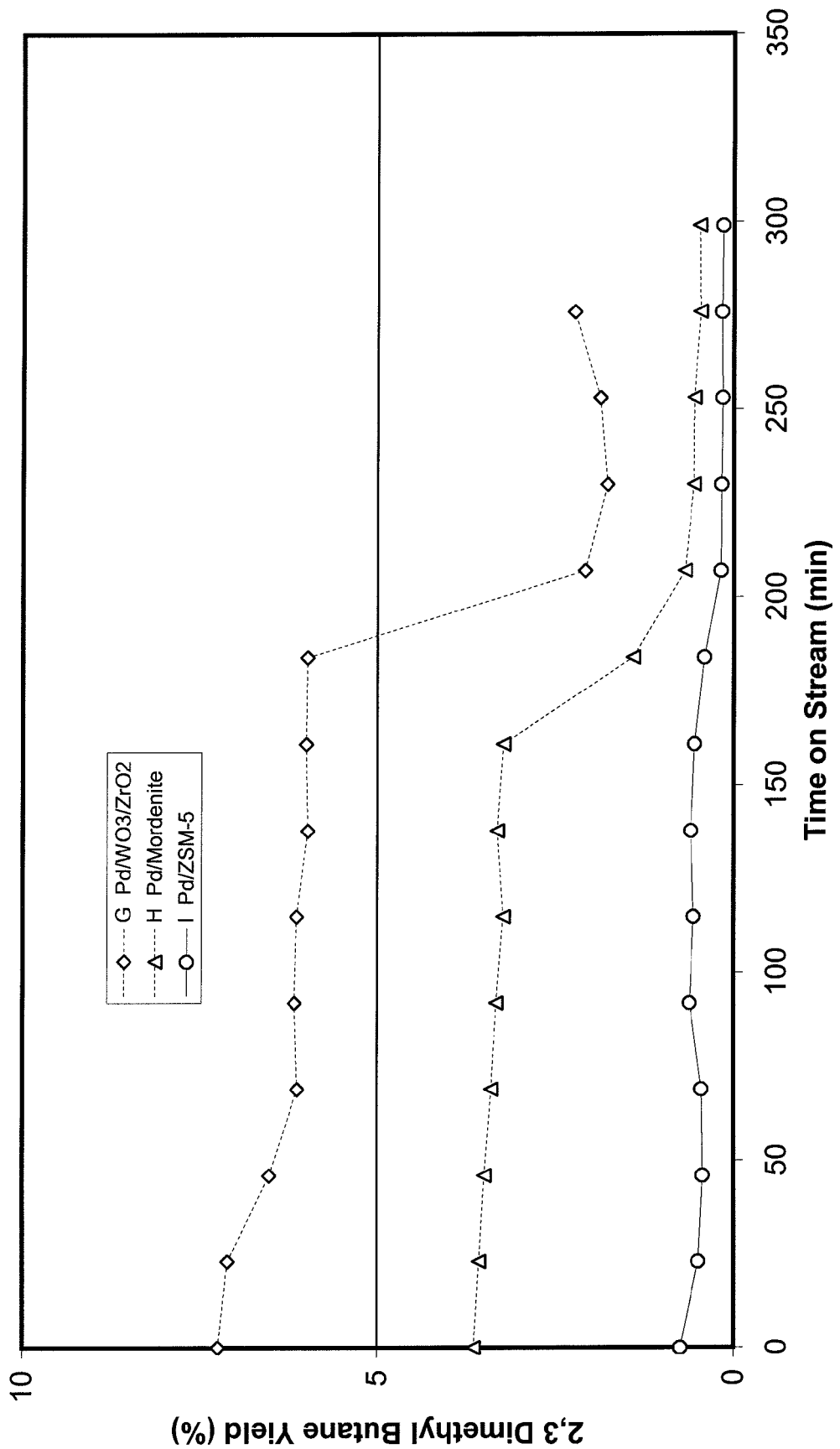
FIG. 7 is a graphic illustration of 2,3 Dimethyl Butane Yield vs. Time on Stream data for three runs wherein palladium containing catalysts were separately used to convert n-hexane.

Conversion results, expressed as n-hexane conversion versus time on stream, are presented in FIG. 5, results of DMB yield versus time on stream are presented in FIG. 6, and results of 2,3 DMB yield versus time on stream are presented in FIG. 7. The results in FIGS. 5-7 demonstrate that the inventive Pd/WO$_3$/ZrO$_2$ Catalyst G is much more effective at converting n-hexane, with much higher DMB and 2,3 DMB yields, than the Pd/Mordenite Control Catalyst H or the Pd/ZSM-5 Control Catalyst I.

Example IV

Inventive Ni/WO$_3$/ZrO$_2$ Catalyst "J"
(2.44 wt. % Ni; 12.3 wt. % W)

Catalyst J was prepared using the same procedure as that for Catalyst B.

Control Ni/Mordenite Catalyst "K"
(2.5 wt. % Ni)

Catalyst K was prepared using the same procedure as that for Catalyst E, but, in place of the aqueous solution of chloroplatinic acid, using an aqueous solution of nickel (II) nitrate.

Control Ni/ZSM-5 Catalyst "L"
(2.5 wt. % Ni)

Catalyst L was prepared using the same procedure as that for Catalyst F, but, in place of the aqueous solution of chloroplatinic acid, using an aqueous solution of nickel (II) nitrate.

A stream of hydrocarbons containing about 5 wt % cyclohexane in n-hexane was separately passed over about eight grams of each of Catalysts J, K and L in a reactor at a rate of about 25 mL/hr (a LHSV of about 2 hr$^{-1}$) Along with the hydrocarbon feed, about 60 sccm of $H_2$ was also charged to the reactor during each run, resulting in a $H_2$/HC molar ratio of about 0.7. The reactor temperature for the Catalyst J run varied from about 204.4° C. at the beginning of each run down to about 176.7° C. after 206 minutes on stream and the pressure was about 200 psig. The reactor temperature for Catalyst K and L runs varied from about 176.7° C. at the beginning of each run up to about 204.4° C. after 72 minutes on stream and the pressure was also about 200 psig.

Figure 8:
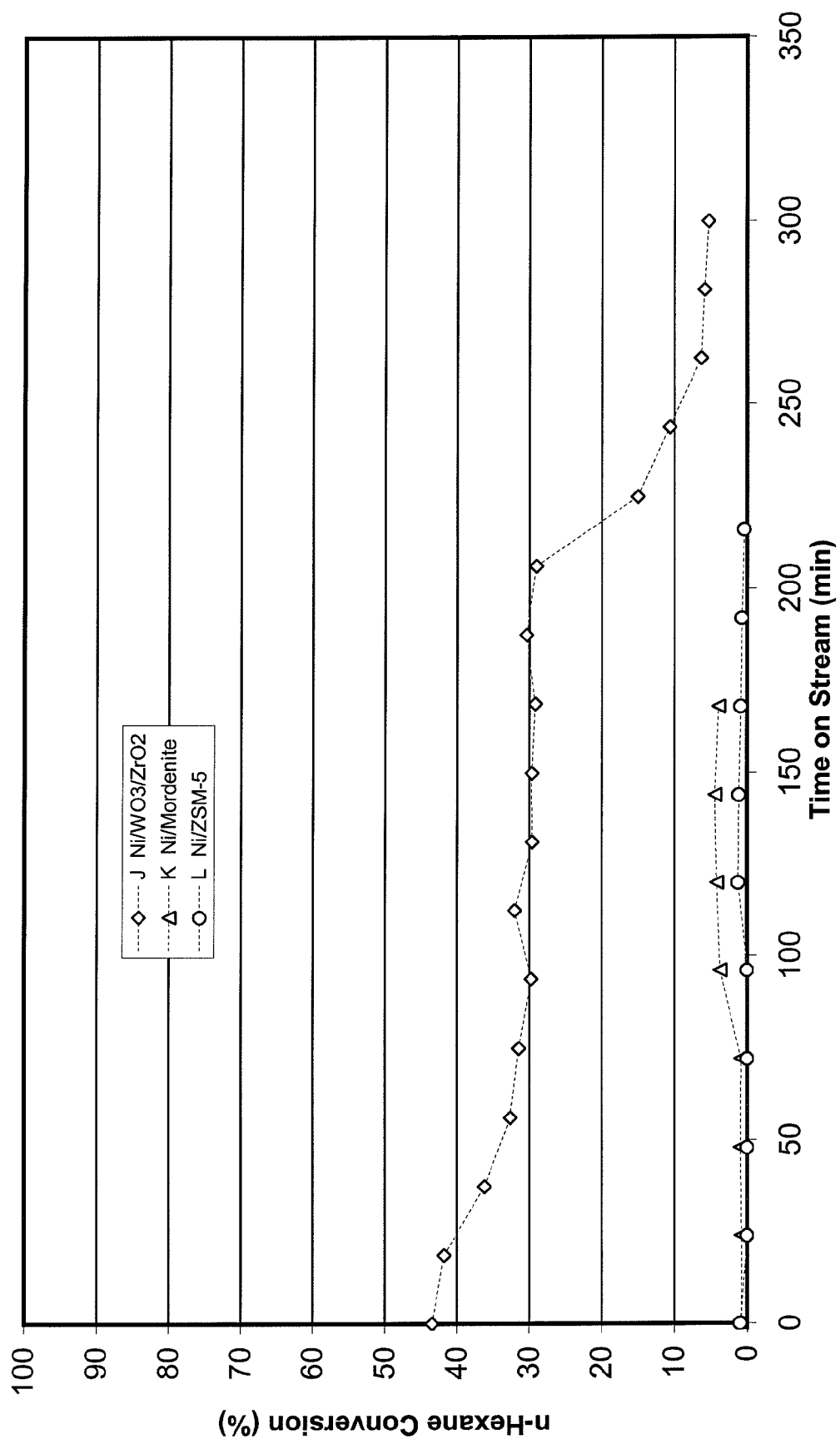
FIG. 8 is a graphic illustration of n-Hexane Conversion vs. Time on Stream data for three runs wherein nickel containing catalysts were separately used to convert n-hexane.
Figure 9:
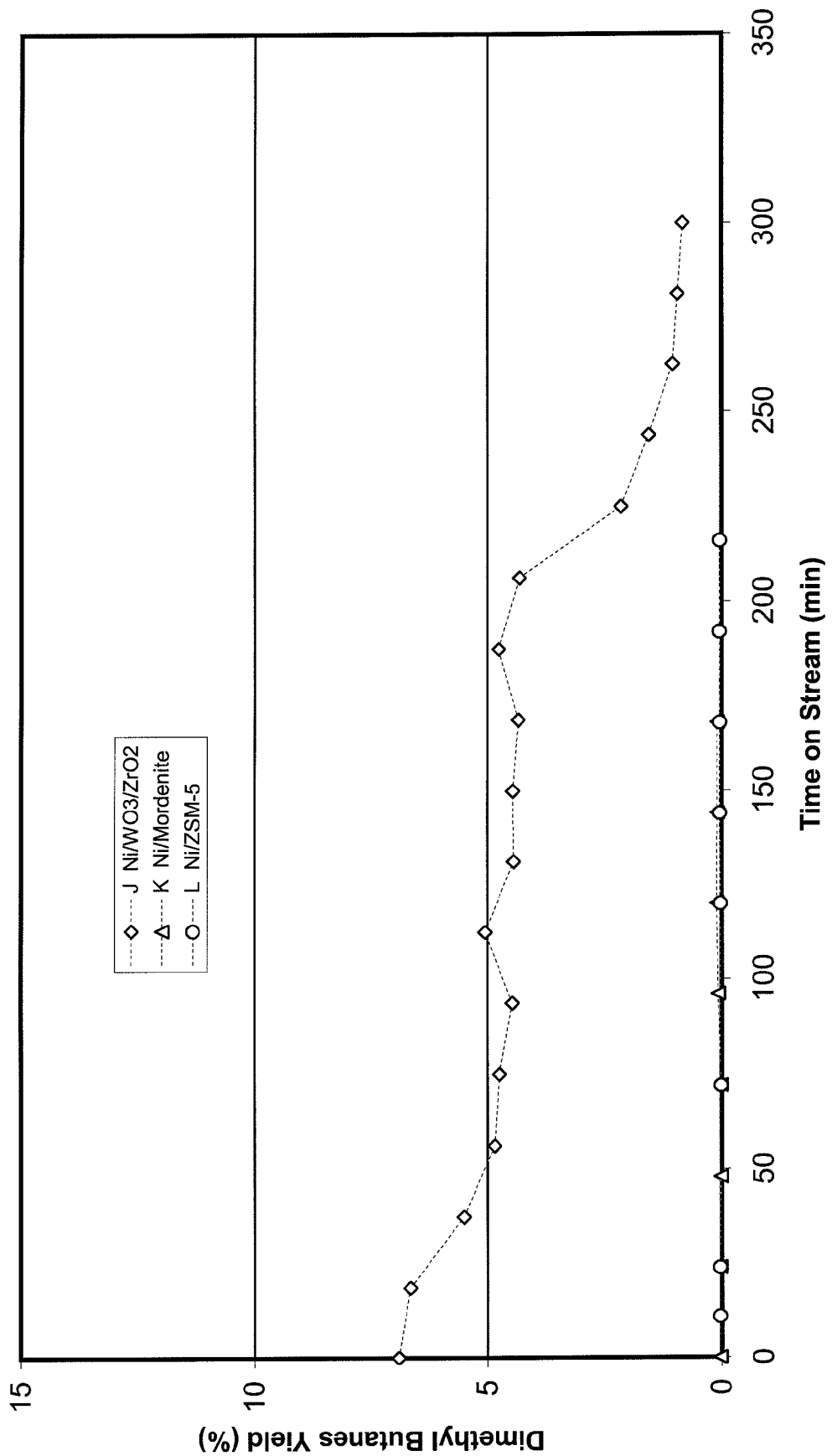
FIG. 9 is a graphic illustration of Dimethyl Butanes Yield vs. Time on Stream data for three runs wherein nickel containing catalysts were separately used to convert n-hexane.
Figure 10:
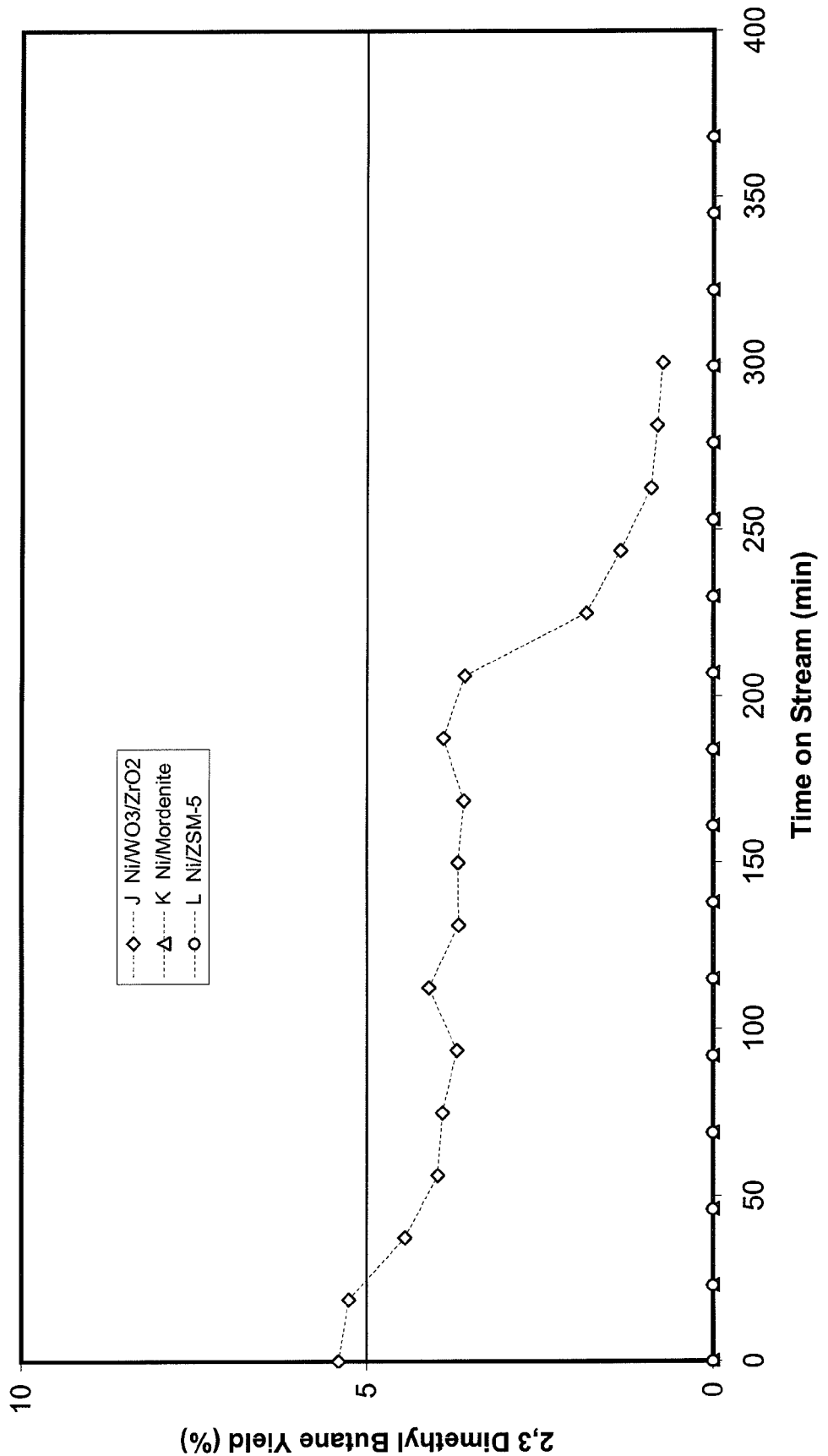
FIG. 10 is a graphic illustration of 2,3 Dimethyl Butane Yield vs. Time on Stream data for three runs wherein nickel containing catalysts were separately used to convert n-hexane.

Conversion results, expressed as n-hexane conversion versus time on stream, are presented in FIG. 8, results of DMB yield versus time on stream are presented in FIG. 9, and results of 2,3 DMB yield versus time on stream are presented in FIG. 10. The results in FIGS. 8-10 demonstrate that the inventive Ni/WO$_3$/ZrO$_2$ Catalyst J is much more effective at converting n-hexane, with much higher DMB and 2,3 DMB yields, than the Ni/Mordenite Control Catalyst K or the Ni/ZSM-5 Control Catalyst L.

Figure 11:
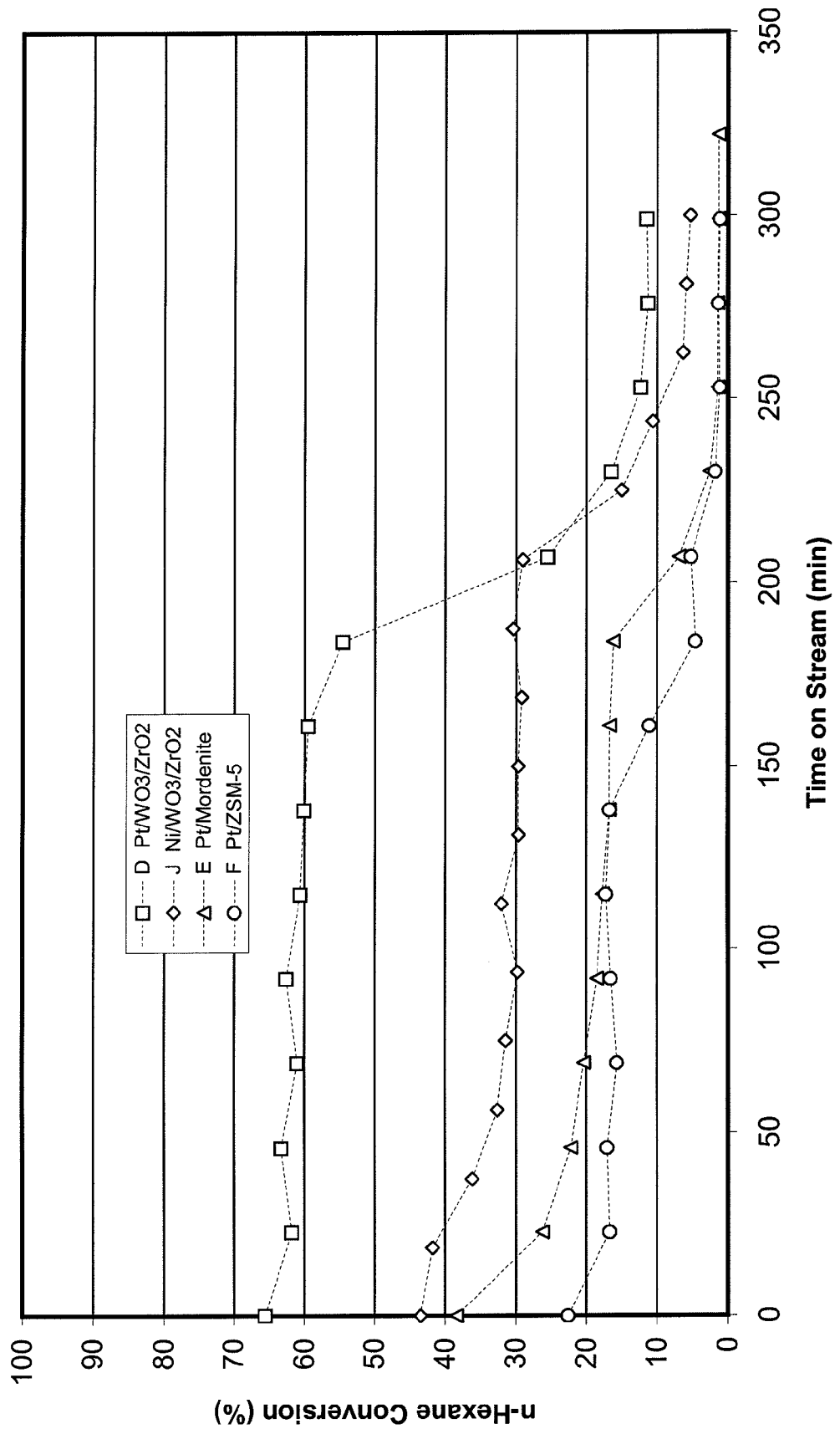
FIG. 11 is a graphic illustration of n-Hexane Conversion vs. Time on Stream data for four runs wherein a nickel containing catalyst and platinum containing catalysts were separately used to convert n-hexane.
Figure 12:
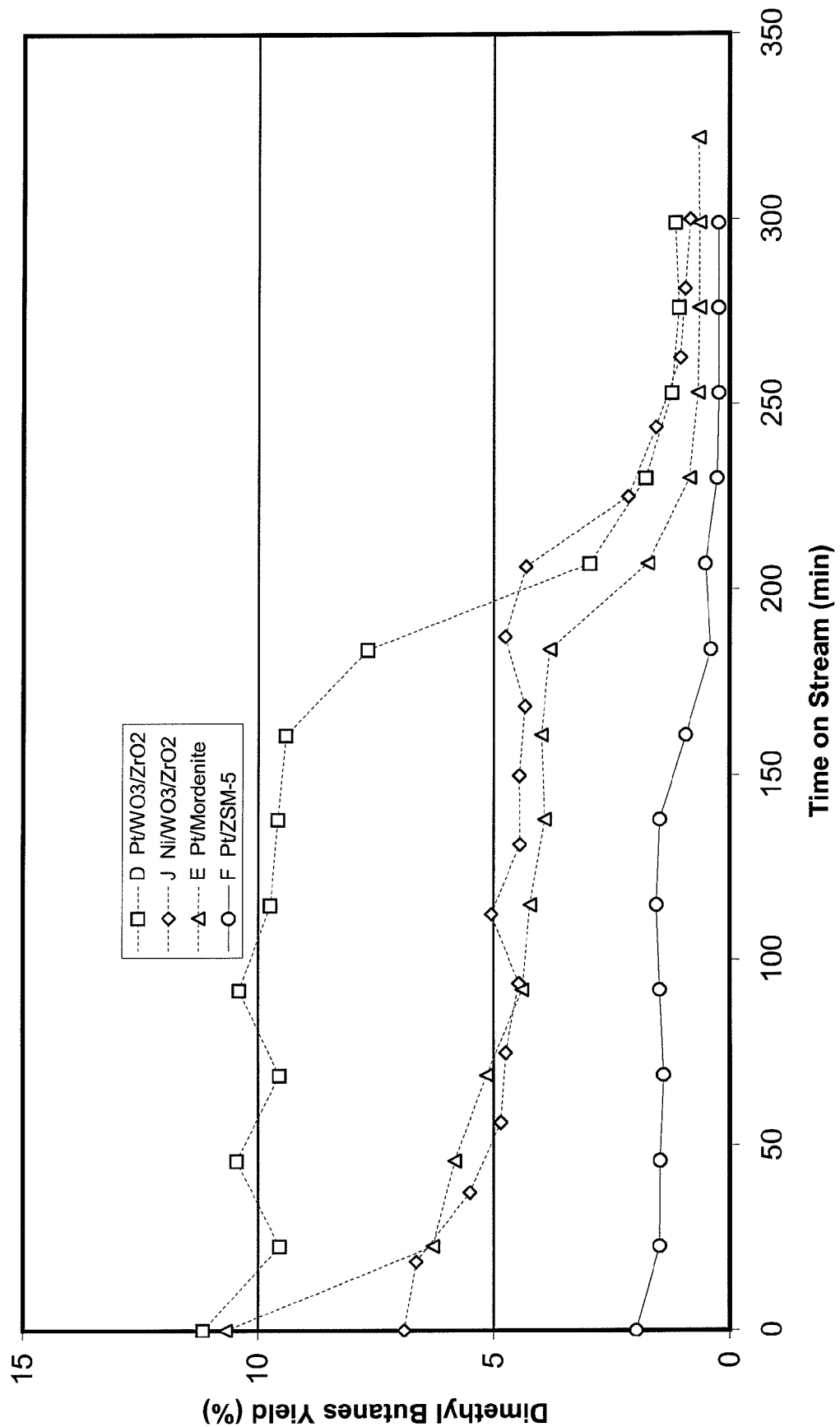
FIG. 12 is a graphic illustration of n-Hexane Conversion vs. Time on Stream data for four runs wherein a nickel containing catalyst and platinum containing catalysts were separately used to convert n-hexane.
Figure 13:
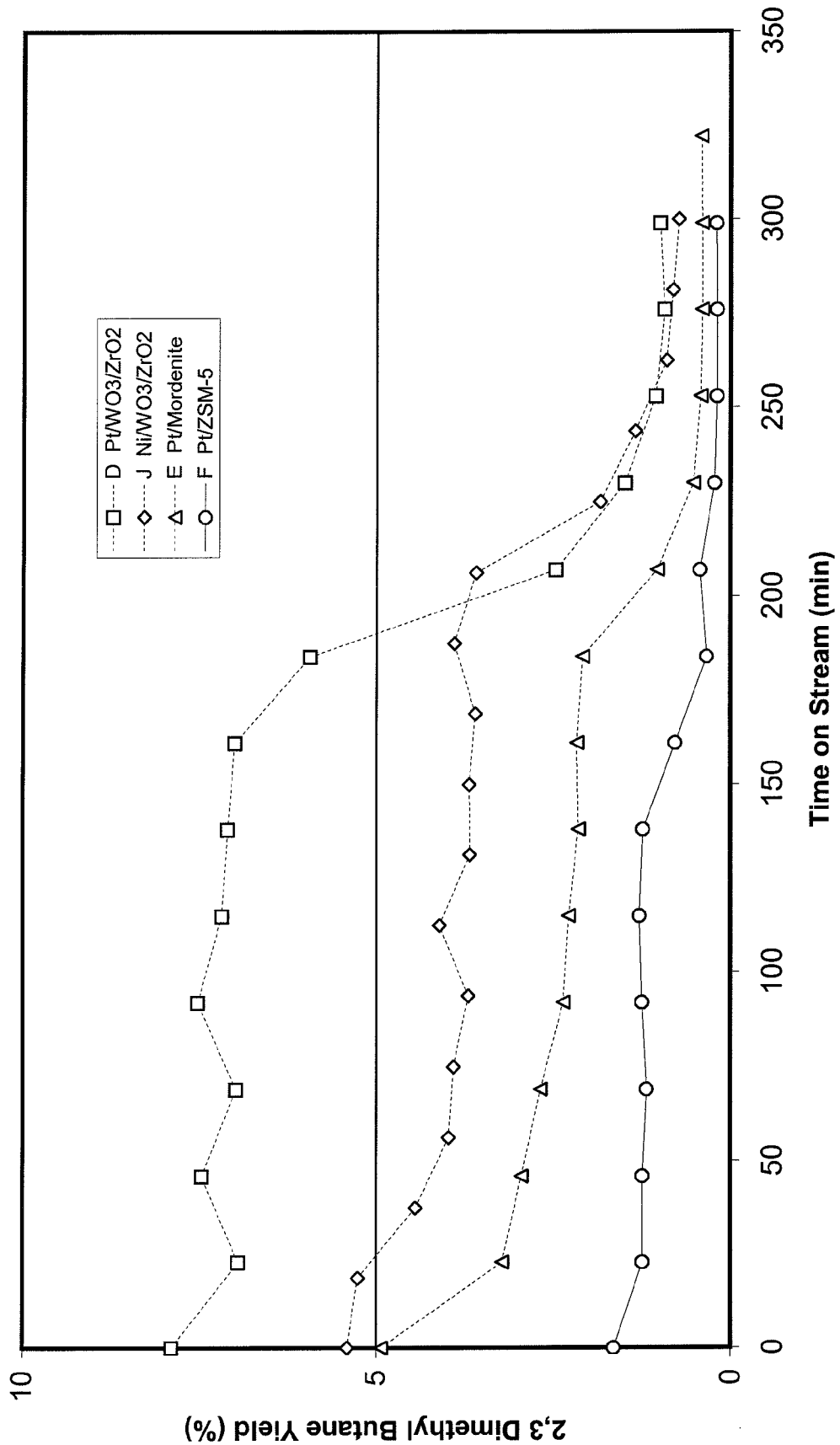
FIG. 13 is a graphic illustration of 2,3 Dimethyl Butane Yield vs. Time on Stream data for four runs wherein a nickel containing catalyst and platinum containing catalysts were separately used to convert n-hexane.

FIGS. 11-13 compare n-hexane conversion, DMB yield, and 2,3 DMB yield, respectively, versus time on stream, for Inventive Catalysts D and J with that for Control Catalysts E and F. The results show that the Pt/WO$_3$/ZrO$_2$ Catalyst D and the Ni/WO$_3$/ZrO$_2$ Catalyst J are much more effective at converting n-hexane, with much higher DMB and 2,3 DMB yields, than the Pt/Mordenite Control Catalyst E or the Pt/ZSM-5 Control Catalyst F.

Table 1 below presents compositional and physical property data for Catalysts D-L (grouped by catalyst type), and Table 2 below presents zirconia, nickel and tungsten data for Inventive Catalysts D(Pt), G(Pd), and J(Ni).

TABLE 1

| Catalyst | Pt, Pd, Ni Loading (wt %) | Tungsten Surface Loading (W/nm$^2$) | Tungsten Loading (wt %) | Hf Impurity (wt %) | SiO$_2$/Al$_2$O$_3$ | Surface Area (m$^2$/g) |
|---|---|---|---|---|---|---|
| D Pt/WO$_3$/ZrO$_2$ | 0.46 | 6.8 | 12.0 | 1.58 | — | 57.6 |
| G Pd/WO$_3$/ZrO$_2$ | 0.29 | 7.4 | 13.0 | 1.40 | — | 57.4 |
| J Ni/WO$_3$/ZrO$_2$ | 2.44 | 7.3 | 12.3 | 1.52 | — | 55.1 |
| E Pt/Mordenite | 0.5 | — | — | — | 20 | 500 |
| H Pd/Mordenite | 0.3 | — | — | — | 20 | 500 |
| K Ni/Mordenite | 2.5 | — | — | — | 20 | 500 |
| F Pt/ZSM-5 | 0.5 | — | — | — | 23 | 425 |
| I Pd/ZSM-5 | 0.3 | — | — | — | 23 | 425 |
| L Ni/ZSM-5 | 2.5 | — | — | — | 23 | 425 |

TABLE 2

| Catalyst | Zirconia (wt %) | Zirconium Tungstate (wt %) | Nickel Tungstate (wt %) | Nickel Oxide (wt %) | Ni/W (Mole) | % Ni as NiWO$_4$ |
|---|---|---|---|---|---|---|
| D Pt/WO$_3$/ ZrO$_2$ | 79.1 | 20.5 | — | — | — | — |
| G Pd/WO$_3$/ ZrO$_2$ | 78.9 | 21.1 | — | — | — | — |
| J Ni/WO$_3$/ ZrO$_2$ | 78.9 | 11.7 | 8.1 | 1.2 | 0.621 | 62.2 |

Example V

Inventive Ni/WO$_3$/ZrO$_2$ Catalysts "M"-"P"

Inventive Catalysts M-P were prepared by the same method of Catalyst B, but with a calcination temperature of 700° C. instead of 498.9° C., and with a relatively low W loading.

Inventive Ni/WO$_3$/ZrO$_2$ Catalyst "Q"

Inventive Catalyst Q was prepared by the same method of Catalyst B, but with a calcination temperature of 700° C. instead of 498.9° C., and with a relatively high W loading.

Inventive Ni/WO$_3$/ZrO$_2$ Catalyst "R"

Inventive Catalyst R was prepared by the same method of Catalyst B, but with a calcination temperature of 800° C. instead of 498.9° C., and with a relatively low W loading.

Inventive Ni/WO$_3$/ZrO$_2$ Catalyst "S"

Inventive Catalyst S was prepared by the same method of Catalyst B, but with a calcination temperature of 900° C. instead of 498.9° C., and with a relatively low W loading.

Additional data for Catalysts M-S is shown in Table 3 below.

Control WO$_3$/ZrO$_2$ Catalyst "T"
(17.8 wt. % W; 700° C. Calcination)

Control Catalyst T was prepared by the same method used to prepare the WO$_3$/ZrO$_2$ material in Example I, but with a calcination temperature of 700° C. instead of 748.9° C.

TABLE 3

| Catalyst | % Ni in NiWO$_4$ | Ni (Wt %) | Hf (Wt %) | W (Wt %) | Ni/W Mole Ratio | ZrO$_2$ (Wt %) |
|---|---|---|---|---|---|---|
| M | 83.2 | 1.379 | 2.069 | 10.75 | 0.40 | 82.1 |
| N | 50.9 | 3.2 | 2.08 | 10.074 | 0.99 | 81.5 |
| O | 13.4 | 4.793 | 1.866 | 10.26 | 1.46 | 78.7 |
| P | 8.0 | 6.352 | 1.903 | 10.236 | 1.94 | 76.6 |
| Q | 100.0 | 3.04 | 1.41 | 16.2 | 0.59 | 69.9 |
| R | 70.3 | 1.878 | 2.116 | 9.544 | 0.62 | 84.1 |
| S | 86.4 | 1.782 | 2.104 | 9.549 | 0.58 | 84.3 |

A stream of hydrocarbons containing about 5 wt % cyclohexane in n-hexane was separately passed over about two grams of each of Catalysts M-R and T (and about four grams of catalyst were used for Catalyst S) in a reactor at a rate of about 25 mL/hr (a LHSV of about 17 hr$^{-1}$ for Catalysts M-R and T, and about 8.5 hr$^{-1}$ for Catalyst S). Along with the hydrocarbon feed for each run, about 60 sccm of H$_2$ was also charged to the reactor during each run, resulting in a H$_2$/HC molar ratio of about 0.7. For one additional run each, the stream of hydrocarbons was passed over about two grams of each of Catalysts Q and T at a flow rate yielding a LHSV of about 2 hr$^{-1}$, and the flow rate of H$_2$ charged to the reactor was adjusted to yield a H$_2$/HC molar ratio of about 0.7. The reactor temperature for all runs was about 287.8° C. and the pressure was about 200 psig.

Figure 14:
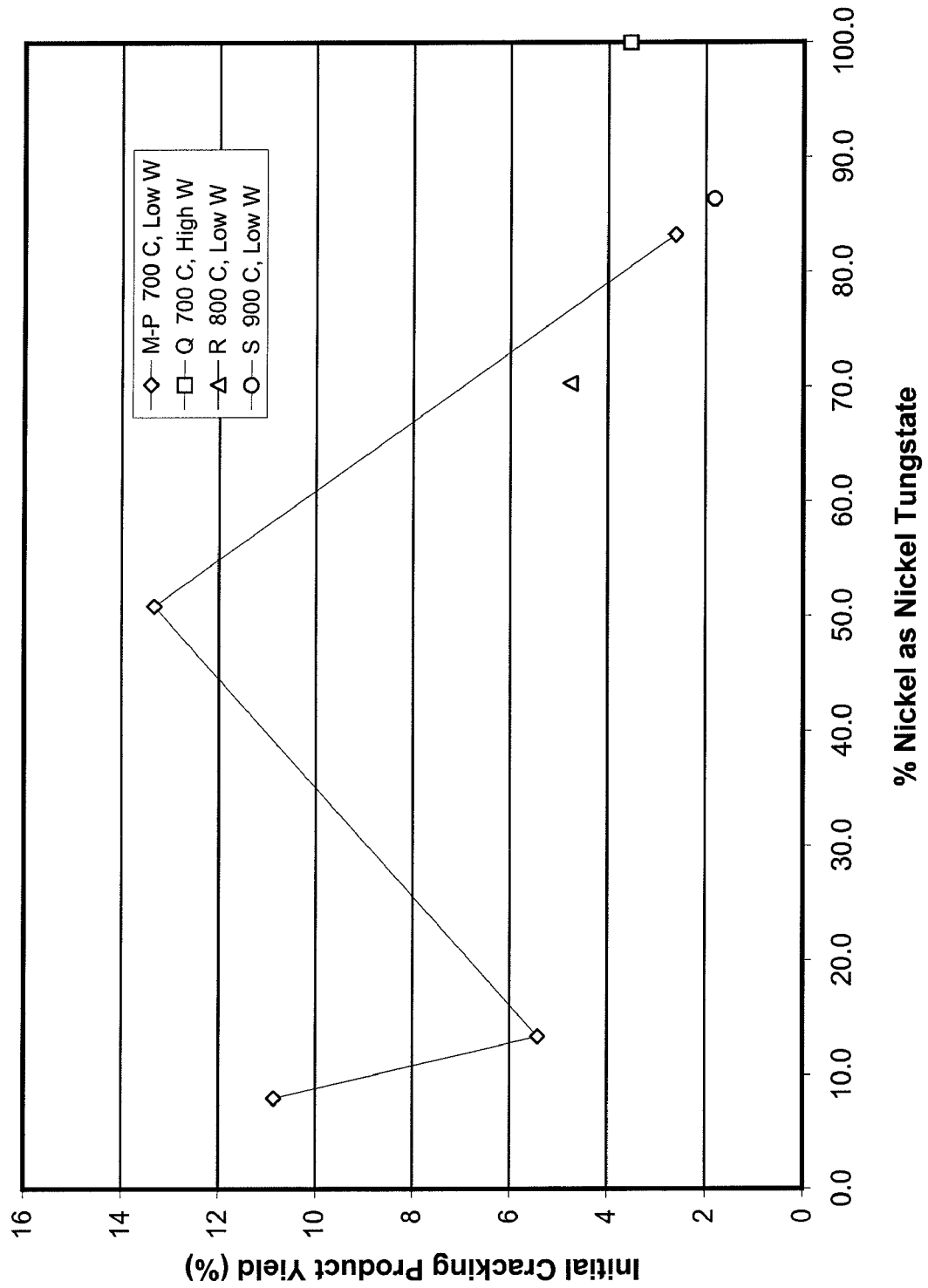
FIG. 14 is a graphic illustration of Initial Cracking Product Yield vs. % Nickel as Nickel Tungstate data for seven runs wherein nickel containing catalysts were separately used to convert n-hexane.

Results of the initial cracking product yield versus % Ni as NiWO$_4$ in the catalyst for Catalysts M-S are presented in FIG. 14. Catalysts M-P are plotted in FIG. 14 as a group labeled "700° C., Low W". The results in FIG. 14 demonstrate that n-hexane conversion over a Ni/WO$_3$/ZrO$_2$ catalyst having a higher % Ni as NiWO$_4$ generally results in much lower initial cracking activity as compared to a Ni/WO$_3$/ZrO$_2$ catalyst having a lower % Ni as NiWO$_4$.

Figure 15:
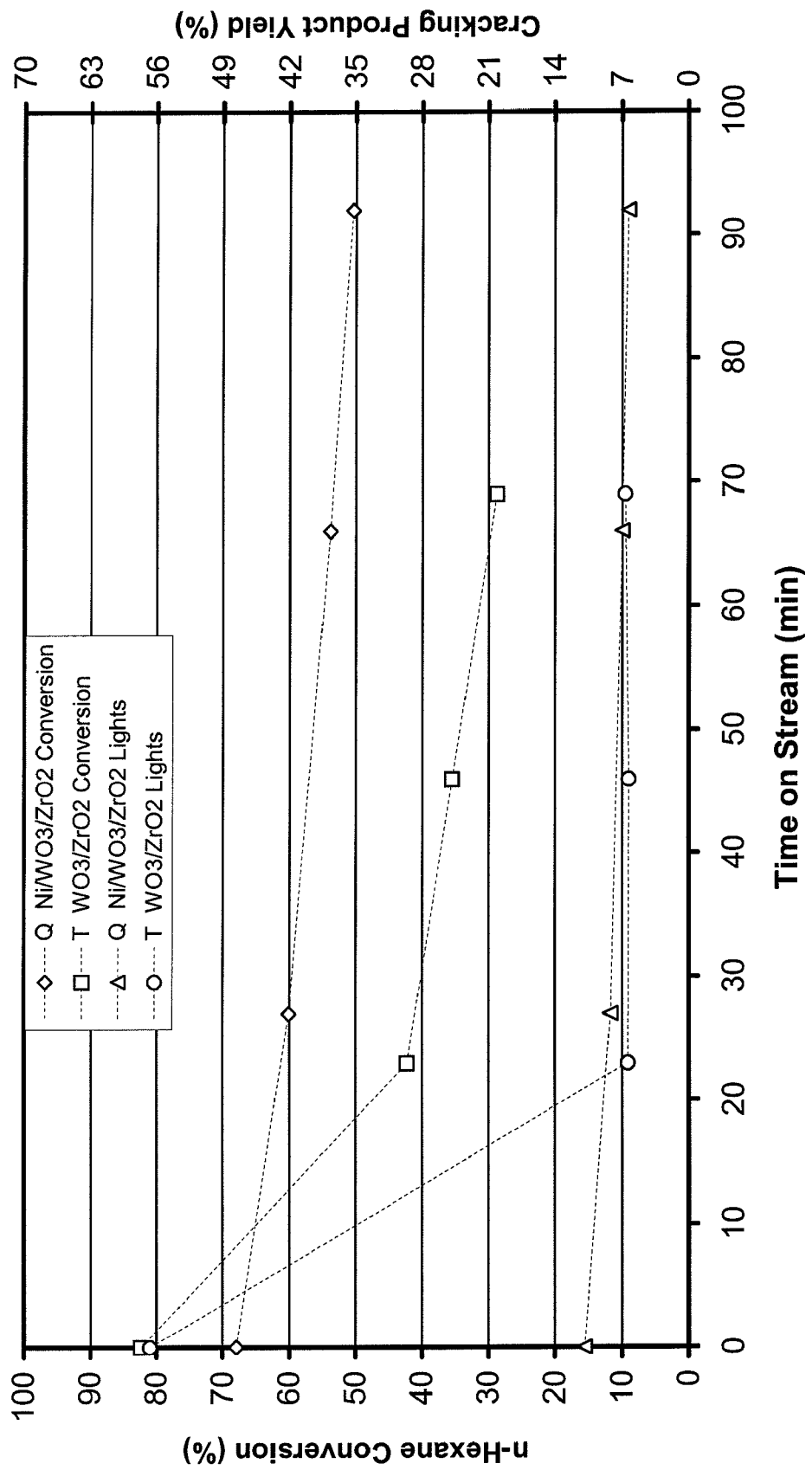
FIG. 15 is a graphic illustration of n-Hexane Conversion vs. Time on Stream data and of Cracking Product Yield vs. Time on Stream data for two runs wherein a nickel containing catalyst and a tungstate zirconia catalyst were separately used to convert n-hexane.
Figure 16:
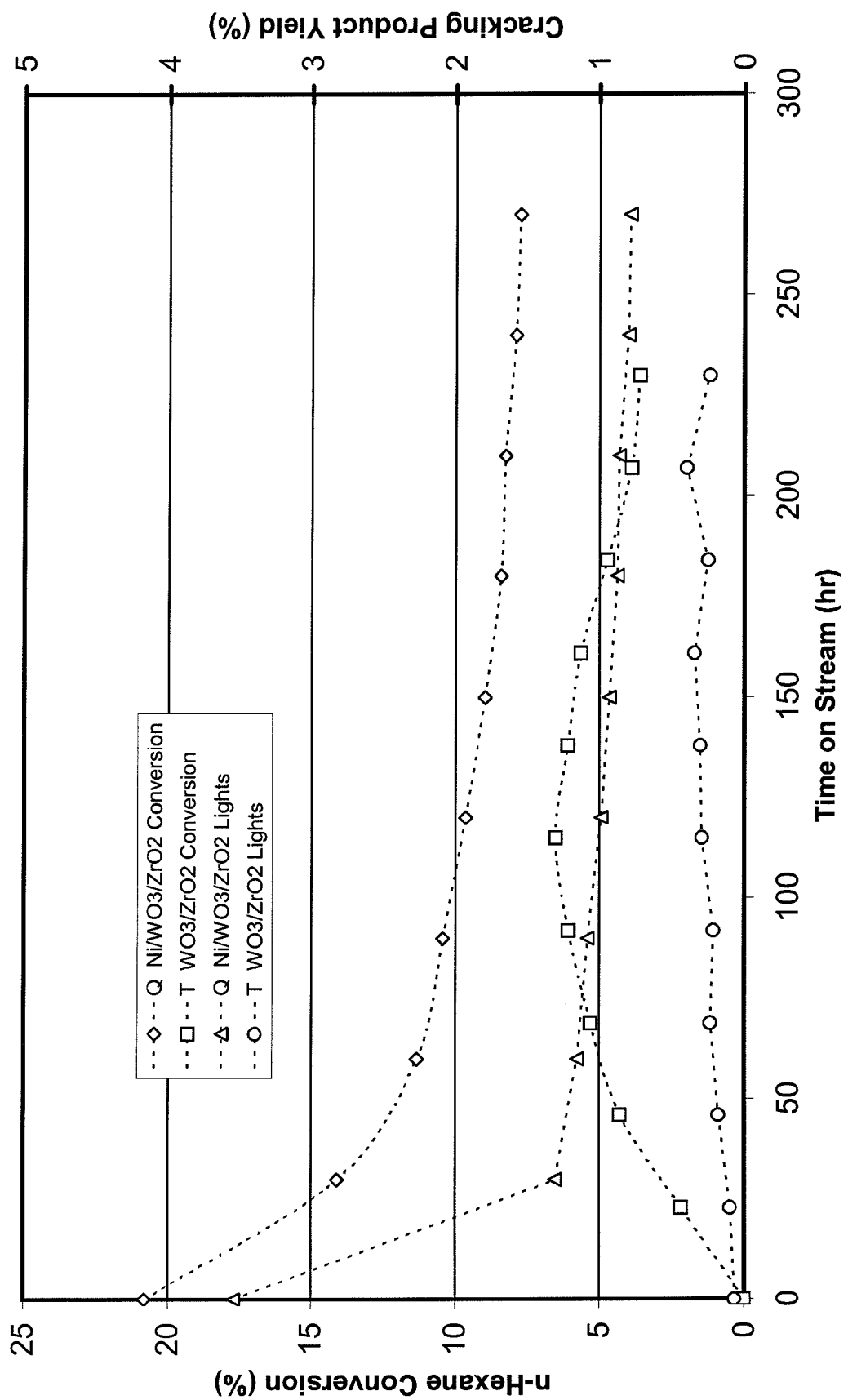
FIG. 16 is a graphic illustration of n-Hexane Conversion vs. Time on Stream data and of Cracking Product Yield vs. Time on Stream data for two runs wherein a nickel containing catalyst and a tungstate zirconia catalyst were separately used to convert n-hexane.

The n-Hexane conversion results and cracking product yield results for the 2 hr$^{-1}$ LHSV run and for the 17 hr$^{-1}$ LHSV run, comparing Catalysts Q and T, are presented in FIGS. 15 and 16, respectively. The results in FIGS. 15 and 16 demonstrate that adding nickel to a WO$_3$/ZrO$_2$ catalyst (as in Catalyst Q) generally results in higher n-hexane conversion as compared to a WO$_3$/ZrO$_2$ catalyst. The results also show that the cracking product yield for catalysts Q and T were similar for the 2 hr$^{-1}$ LHSV run, and, for the 17 hr$^{-1}$ LHSV run, was somewhat higher, but still relatively low, for the Ni/WO$_3$/ZrO$_2$ catalyst (Q) as compared to the WO$_3$/ZrO$_2$ catalyst (T).

Example VI

Ni/WO$_3$/ZrO$_2$ Catalysts "U" and "V"

Catalysts U and V were prepared by the same method of Catalyst A, but with a calcination temperature of 800° C. instead of 498.9° C.

Ni/WO$_3$/ZrO$_2$ Catalysts "W" and "X"

Catalysts W and X were prepared by the same method of Catalyst A, but with a calcination temperature of 900° C. instead of 498.9° C.

Additional data concerning Catalysts U-X, showing the aluminum and hafnium concentrations among other items, is presented in Tables 4 and 5 below.

A stream of hydrocarbons containing about 5 wt % cyclohexane in n-hexane was separately passed over about two grams of each of Catalysts U-X in a reactor at a rate of about 25 mL/hr (a LHSV of about 17 hr$^{-1}$). Along with the hydrocarbon feed, about 60 sccm of H$_2$ was also charged to the reactor during each run, resulting in a H$_2$/HC molar ratio of about 0.7. The reactor temperature was about 287.8° C. and the pressure was about 200 psig.

Results of such n-hexane conversion runs are shown in Table 6 below. These results demonstrate that the presence of Hf and/or Al in the Ni/WO3/ZrO2 catalyst does not have a substantial effect on either initial n-hexane conversion or initial cracking yield.

TABLE 4

| Catalyst | Nickel Loading (wt %) | Tungsten Surface Loading (W/nm²) | Tungsten Loading (wt %) | Aluminum Doping (wt %) | Hafnium Impurity (wt %) | Calcination Temperature (° C.) | Surface Area (m²/g) |
|---|---|---|---|---|---|---|---|
| U Ni/WO₃/ZrO₂ 800° C. Calcin. | 2.78 | 10.89 | 16.2 | — | — | 800 | 48.9 |
| W Ni/WO₃/ZrO₂ 900° C. Calcin. | 2.33 | 17.11 | 16.9 | — | — | 900 | 32.4 |
| V Ni/WO₃/ZrO₂(Hf) 800° C. Calcin. | 2.26 | 13.17 | 16.7 | — | 1.41 | 800 | 41.6 |
| X Ni/WO₃/ZrO₂(1Al, Hf) 900° C. Calcin. | 2.59 | 17.79 | 16.6 | 1.07 | 1.35 | 900 | 30.6 |

TABLE 5

| Catalyst | Zirconia (wt %) | Tungsten Oxide (wt %) | Nickel Tungstate (wt %) | Nickel Oxide (wt %) | Ni/W (Mole) | % Ni as NiWO₄ |
|---|---|---|---|---|---|---|
| U Ni/WO₃/ZrO₂ 800° C. Calcin. | 83 | 2.4 | 14.6 | — | 0.54 | 100 |
| W Ni/WO₃/ZrO₂ 900° C. Calcin. | 80 | 10.5 | 9.4 | 0.3 | 0.43 | 88.4 |
| V Ni/WO₃/ZrO₂ (Hf) 800° C. Calcin. | 81 | 6.9 | 12 | — | 0.42 | 100 |
| X Ni/WO₃/ZrO₂ (1Al, Hf) 900° C. Calcin. | 82 | 6.4 | 11.7 | — | 0.49 | 100 |

TABLE 6

| Catalyst | Initial n-Hexane Conversion (%) | Initial Cracking Yield (%) |
|---|---|---|
| U Ni/WO₃/ZrO₂ 800° C. Calcin. | 21.6 | 0.31 |
| W Ni/WO₃/ZrO₂ 900° C. Calcin. | 25.0 | 3.34 |
| V Ni/WO₃/ZrO₂ (Hf) 800° C. Calcin. | 22.3 | 3.10 |
| X Ni/WO₃/ZrO₂ (1Al, Hf) 900° C. Calcin. | 20.3 | 1.87 |

While this invention has been described in detail for the purpose of illustration, it should not be construed as limited thereby but intended to cover all changes and modifications within the spirit and scope thereof.

That which is claimed:

1. An isomerization process comprising contacting a hydrocarbon feed comprising n-hexane and less than about 10 volume % naphthenic hydrocarbons with a catalyst at isomerization conditions for isomerization of at least a portion of said n-hexane to a product comprising iso-hexane; wherein said catalyst is prepared by the following method:
   (a) incorporating tungsten on a zirconium hydroxide solid by incipient wetness impregnation using an aqueous solution of a tungsten compound to form tungsten impregnated zirconium hydroxide;
   (b) drying and calcining said tungsten impregnated zirconium hydroxide to form a first dried and calcined material;
   (c) sizing said dried and calcined material to particle sizes between about 150 and about 600 microns to form a sized material;
   (d) incorporating a Group VIII metal selected from the group consisting of nickel, platinum and palladium, and combinations thereof, on said sized material by incipient wetness impregnation using an aqueous solution of a Group VIII metal compound comprising said Group VIII metal to form a Group VIII metal impregnated tungsten/zirconia material;
   (e) drying and calcining said Group VIII metal impregnated tungsten/zirconia material to form a second dried and calcined material;
   (f) contacting said second dried and calcined material with hydrogen in a reducing environment to form said catalyst which comprises tungsten, zirconia and a Group VIII metal selected from the group consisting of nickel, platinum and palladium, and combinations thereof, and wherein said zirconium hydroxide solid of step (a) contains sufficient aluminum to result in said catalyst containing between about 0.1 and about 3 weight % aluminum.

2. A process in accordance with claim 1 wherein said product comprises an iso-hexane selected from the group consisting of 2,2-dimethylbutane, 2,3-dimethylbutane, 2-methylpentane, 3-methylpentane, and combinations thereof.

3. A process in accordance with claim 1 wherein said product comprises 2,3-dimethylbutane.

4. A process in accordance with claim 1 wherein said isomerization conditions include a temperature in the range of from about 160° C. to about 300° C., a pressure in the range of from about 150 to about 250 psig, a liquid hourly space velocity of about 0.5 to about 20 hr$^{-1}$, and a hydrogen to hydrocarbon molar ratio of at least about 0.1.

5. A process in accordance with claim 1 wherein said isomerization conditions include a temperature in the range of from about 177° C. to about 288° C., a pressure in the range of from about 190 to about 210 psig, a liquid hourly space velocity of about 0.5 to about 10 hr$^{-1}$, and a hydrogen to hydrocarbon molar ratio of at least about 0.5.

6. A process in accordance with claim 1 wherein said isomerization conditions include a temperature in the range of from about 177° C. to about 230° C., a pressure in the range of from about 190 to about 210 psig, a liquid hourly space velocity of about 0.5 to about 4 hr$^{-1}$, and a hydrogen to hydrocarbon molar ratio of at least about 0.5.

7. A process in accordance with claim 1 wherein said hydrocarbon feed comprises at least about 80 weight % n-hexane.

8. A process in accordance with claim 1 wherein said hydrocarbon feed comprises at least about 90 weight % n-hexane.

9. A process in accordance with claim 1 wherein said tungsten compound is ammonium metatungstate.

10. A process in accordance with claim 1 wherein said calcining of step b) is in the presence of oxygen and at a temperature in the range of from about 600° C. to about 900° C.; and wherein said calcining of step e) is in the presence of oxygen and at a temperature in the range of from about 300° C. to less than or equal to about said calcining temperature in step b).

11. A process in accordance with claim 10 wherein said Group VIII metal compound comprises nickel; wherein the molar ratio of nickel to tungsten in said second dried and calcined material is at most about 0.65; and wherein at least about 70% of the nickel of said second dried and calcined material is in the form of nickel tungstate.

12. A process in accordance with claim 1 wherein said Group VIII metal compound is selected from the group consisting of nickel (II) nitrate, chloroplatinic acid, tetraamine palladium (II) nitrate, diammineplatinum (II) nitrate, palladium (II) nitrate, and combinations thereof.

13. A process in accordance with claim 1 wherein said catalyst comprises between about 60 and about 95 weight % zirconia; between about 5 and about 40 weight % tungsten; and between about 0.01 and about 5 weight % of said Group VIII metal.

14. A process in accordance with claim 1 wherein said catalyst comprises between about 70 and about 90 weight % zirconia; between about 5 and about 35 weight % tungsten; and between about 0.01 and about 5 weight % of said Group VIII metal.

15. A process in accordance with claim 1 wherein said catalyst comprises between about 75 and about 90 weight % zirconia; between about 10 and about 20 weight % tungsten; and between about 0.1 and about 5 weight % of said Group VIII metal.

16. A process in accordance with claim 13 wherein said Group VIII metal compound comprises nickel and said catalyst comprises between about 1.5 and about 5 weight % nickel.

17. A process in accordance with claim 13 wherein said Group VIII metal, of said Group VIII metal compound, is selected from the group consisting of platinum, palladium, or combinations thereof and wherein said catalyst comprises between about 0.1 and about 0.5 weight % of said Group VIII metal.

18. A process in accordance with claim 1 wherein said reducing environment of step (f) comprises a temperature in the range of from about 350 to about 400° C., and a pressure in the range of from about 150 psig to about 250 psig.

19. A process in accordance with claim 1 wherein said hydrocarbon feed is further characterized to comprise less than about 5 volume % naphthenic hydrocarbons.

20. A process in accordance with claim 1 wherein said zirconium hydroxide solid of step (a) contains sufficient hafnium to result in said catalyst containing between about 0.1 and about 2 weight % hafnium.

* * * * *